(12) United States Patent
Park et al.

(10) Patent No.: US 7,648,777 B2
(45) Date of Patent: Jan. 19, 2010

(54) BLUE ELECTROLUMINESCENT COMPOUND AND ORGANIC ELECTROLUMINESCENT DEVICE USING THE SAME

(75) Inventors: Sang-Hoon Park, Seongnam-si (KR); Tae-Yong Noh, Gunpo-si (KR); O-Hyun Kwon, Seoul (KR); Sang-Yeol Kim, Gwacheon-si (KR); Jhun-Mo Son, Yongin-si (KR); Sung-Hun Lee, Seoul (KR)

(73) Assignee: Samsung Mobile Display Co., Ltd., Yongin, Gyunggi-Do (KR)

( * ) Notice: Subject to any disclaimer, the term of this patent is extended or adjusted under 35 U.S.C. 154(b) by 490 days.

(21) Appl. No.: 11/336,877

(22) Filed: Jan. 23, 2006

(65) Prior Publication Data

US 2006/0166038 A1   Jul. 27, 2006

(30) Foreign Application Priority Data

Jan. 21, 2005   (KR)   ...................... 10-2005-0005810

(51) Int. Cl.
  *H01L 51/54* (2006.01)
  *C09K 11/06* (2006.01)
  *C07D 265/38* (2006.01)
  *C07D 279/18* (2006.01)

(52) U.S. Cl. .................. 428/690; 428/917; 544/35; 544/73; 544/102; 568/12; 313/504; 313/506; 257/40; 257/E51

(58) Field of Classification Search ........................ None
See application file for complete search history.

(56) References Cited

U.S. PATENT DOCUMENTS

| 5,922,481 | A | * | 7/1999 | Etzbach et al. | ............... 428/690 |
| 6,169,163 | B1 | | 1/2001 | Woo et al. | |
| 6,249,369 | B1 | * | 6/2001 | Theiste et al. | ............... 359/265 |
| 6,984,461 | B2 | * | 1/2006 | Son et al. | ..................... 428/690 |
| 2004/0072989 | A1 | * | 4/2004 | Son et al. | ..................... 528/397 |

FOREIGN PATENT DOCUMENTS

| DE | 10143249 | * | 3/2003 |
| WO | WO2006/041263 | * | 4/2006 |

OTHER PUBLICATIONS

Kim et al., Thin Solid Films, 509, (2006), p. 132-136.*
Kramer et al., Tetrahedron Letters, 42, (2001), p. 8619-8624.*
Sailer et al., J. Org. Chem., (2003), 68, p. 7509-7512.*
Shine et al., J. Org. Chem., vol. 44, No. 19, (1979), p. 3310-3316.*
Lai et al., J. Am. Chem. Soc., (2003), 125, p. 12631-12639.*
Machine English translation for DE10143249, publication date Mar. 20, 2003.*

(Continued)

*Primary Examiner*—Dawn Garrett
(74) *Attorney, Agent, or Firm*—Robert E. Bushnell, Esq.

(57) ABSTRACT

An organic electroluminescent compound and an organic electroluminescent device using the same. The organic electroluminescent compound having Formula 1 can be used as blue electroluminescent compound. The organic electroluminescent device using the organic electroluminescent compound having Formula 1 has improved luminous efficiency and color purity.

10 Claims, 5 Drawing Sheets

OTHER PUBLICATIONS

Office action from the Patent Office of the People's Republic of China issued in Applicant's corresponding Chinese Patent Application No. 2006100060120 dated Jun. 5, 2009.

Shine at al., "Ion Radicals. 44, Reactions with 10-Phenylphenoxazine Cation Radical Perchlorate", vol. 44. No. 19. pp. 3310-3316, Dec. 31, 1979.

Kramer et at, "First synthesis and electronic properties of (hetero)aryl bridged and directly lined redox active phenothiazinyl dyads and triads", vol. 42, pp. 8610-8624, Dec. 31, 2001.

Saller at al., "Practical Synthesis of Iodo Phenothiazines. A Facile Access to Electrophore Building Blocks", vol. 68 pp. 7509-7512, Dec. 31, 2003.

* cited by examiner

BLUE ELECTROLUMINESCENT COMPOUND AND ORGANIC ELECTROLUMINESCENT DEVICE USING THE SAME

CROSS-REFERENCE TO RELATED PATENT APPLICATIONS AND CLAIM OF PRIORITY

This application claims the benefit of Korean Patent Application No. 10-2005-0005810, filed on Jan. 21, 2005, in the Korean Intellectual Property Office, the disclosure of which is incorporated herein in its entirety by reference.

BACKGROUND OF THE INVENTION

1. Field of the Invention

The present invention relates to a blue electroluminescent compound and an organic electroluminescent device using the same, and more particularly, to a blue electroluminescent compound containing a phenoxazine-based unit and an organic electroluminescent device having improved luminous efficiency and color purity by using the blue electroluminescent compound as a light-emitting component.

2. Description of the Related Art

Organic electroluminescent devices are active matrix emission type display devices in which, when an electrical current is applied to a fluorescent or phosphorescent organic compound layer (hereinafter, referred-to as an organic layer), electrons and holes are combined in the organic layer to emit light. Organic electroluminescent devices are light and comprise simple components and thus may be manufactured in a simplified process, and also have a wide view angle and display high quality images. Further, they can display high quality moving pictures with high color purity, and can be suitably used for portable electronic devices with low power consumption and low driving voltage.

Organic electroluminescent display devices can use either low or high molecular weight compounds, depending on characteristics of materials for forming organic layers and manufacture.

Many studies have been made about high molecular weight compounds since the discovery of the electroluminescence of poly(1,4-phenylenevinylene)(PPV), a π-conjugated polymer by Cambridge group in 1990. π-Conjugated polymers have an alternating chemical structure of single bonds (or σ bonds) and double bonds (or π bonds), so that the polymers have delocalized π electrons capable of freely moving along with the polymer chain. The π-conjugated polymers have semi-conductive properties, and thus the whole visible light region corresponding to the HOMO-LUMO (highest occupied molecular orbital-lowest occupied molecular orbital) energy band-gap of polymers can be easily obtained through molecular design of the π-conjugated polymer, when the polymers are employed in an electroluminescent layer of an electroluminescent device. In addition, a thin film of polymer can simply be formed by spin coating or printing. Accordingly, the manufacturing process is very simple and cost-effective. Furthermore, the mechanical properties of a thin film of a π-conjugated polymer are excellent due to its high glass transition temperature. However, the device using high molecular weight compounds has several problems, including low color purity, high driving voltage, and low efficiency. Many studies have been made to overcome these problems. For example, U.S. Pat. No. 6,169,163 describes a method of copolymerizing fluorene-containing polymers to improve electroluminescent characteristics of organic electroluminescent devices. However, the improvement achieved is not satisfactory.

In manufacturing the device using low molecular weight compounds, an organic layer can be formed by vacuum deposition, the light-emitting materials can be easily purified to a high degree, and color pixels can be easily obtained. For practical application of the devices using low molecular weight compounds, however, there is still open for improvement in quantum efficiency and color purity, and a need to prevent crystallization of thin layers. Various studies on such electroluminescent displays using low molecular weight compounds have been actively undertaken, especially in Japan and the U.S.A. For example, Idemitsu-Kosan Co., Ltd. of Japan first exhibited in 1997 a 10-inch full color organic electroluminescent display using a color-changing medium. Pioneer Corporation of Japan presented a 5-inch passive matrix (PM) full color organic electroluminescent display. Recently, Pioneer Corporation and Motorola Inc. have arrived at an agreement concerning the mass production of cellular phones with an organic electroluminescent display, thus low molecular weight electroluminescent displays will be commercially viable in the near future.

Accordingly, there is an increasing need for a low molecular weight light-emitting compound which can simply form a thin film by vacuum deposition and spin coating or printing, similar to a high molecular weight compound, be used in dry and wet processes, and have an excellent blue light-emitting property.

SUMMARY OF THE INVENTION

The present invention provides a light-emitting compound which can easily transport charges, be used in dry and wet processes and have an excellent blue light-emitting property, and an organic electroluminescent device having improved driving characteristics, particularly color purity by using the light-emitting compound.

According to an aspect of the present invention, there is provided an organic electroluminescent compound having Formula 1:

(1)

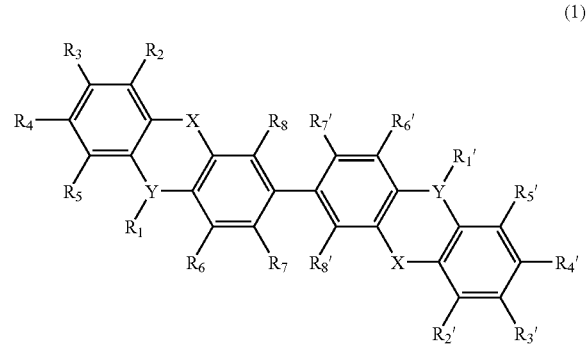

wherein each of $R_1$ through $R_8$ and $R_1'$ through $R_8'$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group, X is O, S, or Se, and Y is N or P.

According to another aspect of the present invention, there is provided an organic electroluminescent device comprising an organic layer between a pair of electrodes, wherein the organic layer contains the organic electroluminescent compound.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
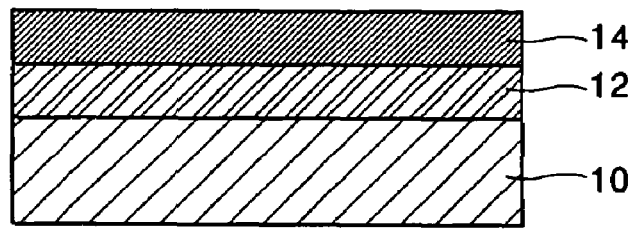
FIGS. 1A through 1F are schematic cross-sectional views of organic electroluminescent devices according to embodiments of the present invention.

Hereinafter, embodiments of the present invention will be described in more detail.

An organic electroluminescent dimer compound according to an embodiment of the present invention has a high charge transport capability, particularly hole transport capability, can be used in dry and wet processes, and has an excellent blue light-emitting property.

The organic electroluminescent compound has Formula 1:

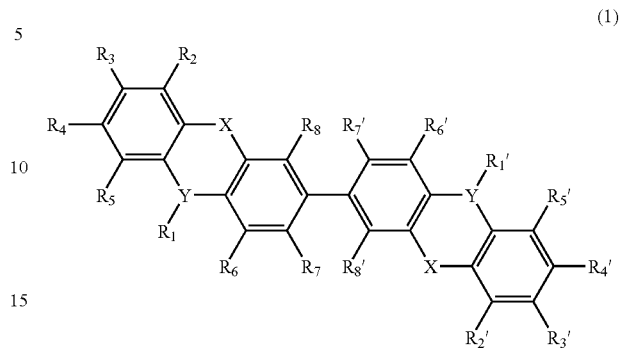

(1)

wherein each of $R_1$ through $R_8$ and $R_1'$ through $R_8'$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group;

X is O, S, or Se; and

Y is N or P.

Preferably, each of $R_1$ through $R_8$ and $R_1'$ through $R_8'$ in Formula 1 may be independently selected from the following Formulae (1a) through (1h):

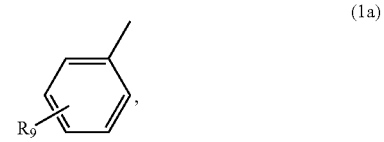

(1a)

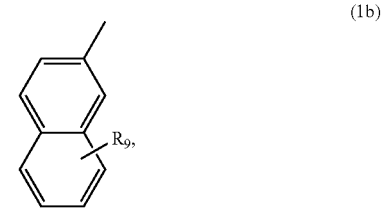

(1b)

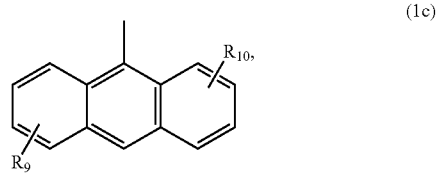

(1c)

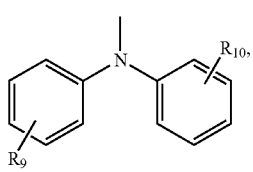
(1d)

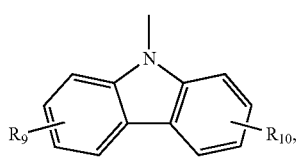
(1e)

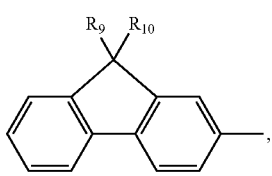
(1f)

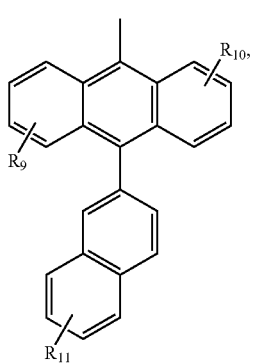
(1g)

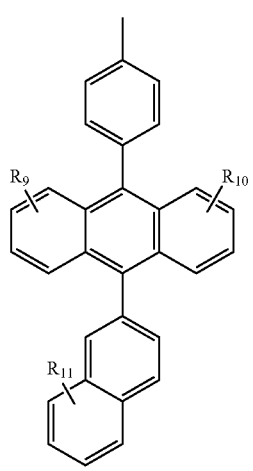
(1h)

wherein each of $R_9$, $R_{10}$, and $R_{11}$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group.

The organic electroluminescent compound may be a phenoxazine-based compound having Formula 2:

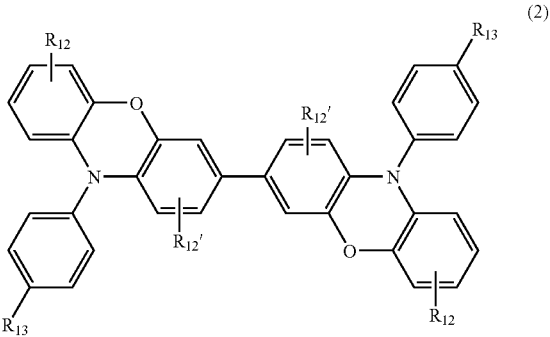
(2)

wherein each of $R_{12}$, $R_{12}'$ and $R_{13}$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group.

The organic electroluminescent compound according to an embodiment of the present invention may have the characteristics required for a light-emitting material by controlling substituents thereof. For example, in Formula 2, electronic and optical properties can be controlled by linking a benzene ring to nitrogen and mechanical properties and a film forming property can be controlled and processibity can be increased by linking one or some of various sustituents, for example, $R_{13}$, to the benzene ring.

Specific examples of the organic electroluminescent compound according to an embodiment of the present invention include organic electroluminescent compounds having Formulae 3 through 9:

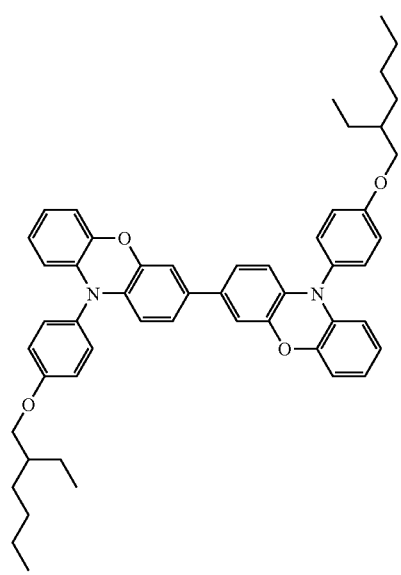
(3)
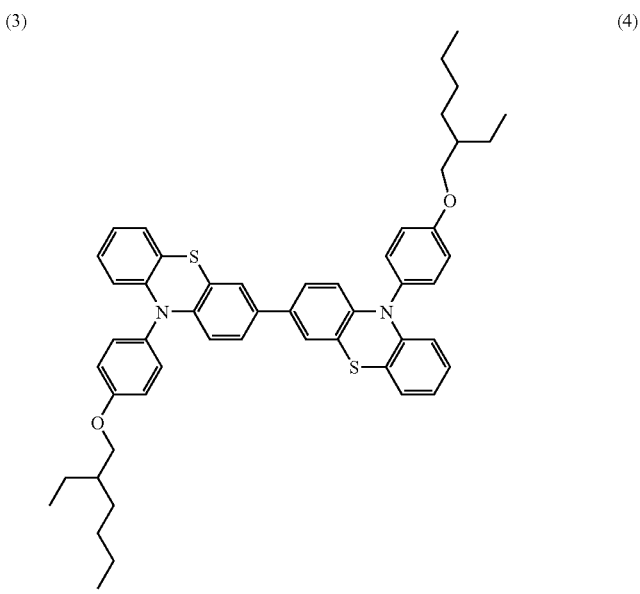
(4)
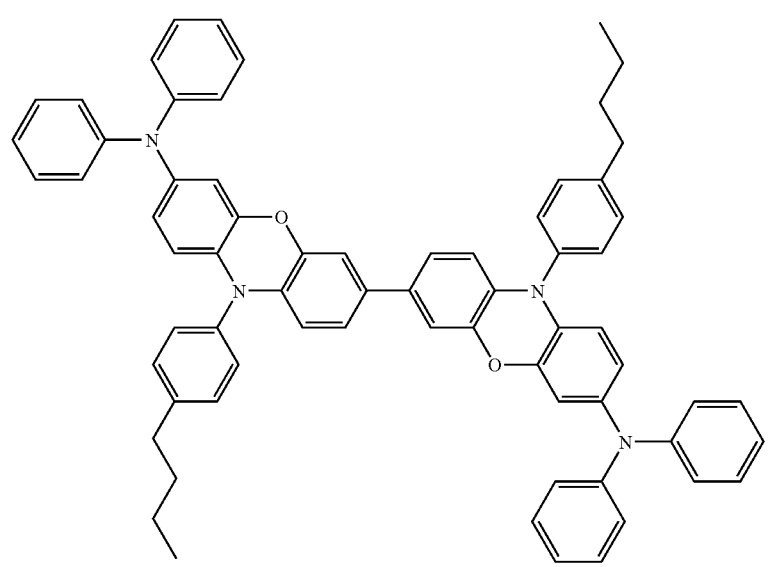
(5)
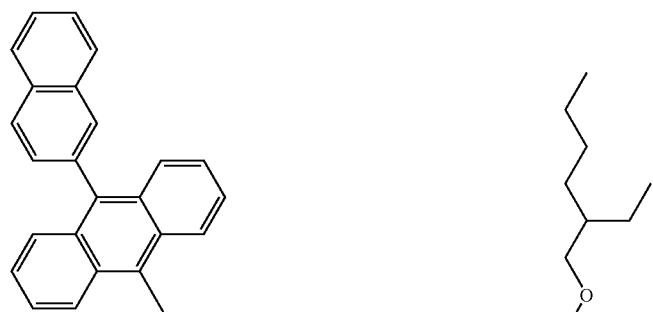
(6)

-continued
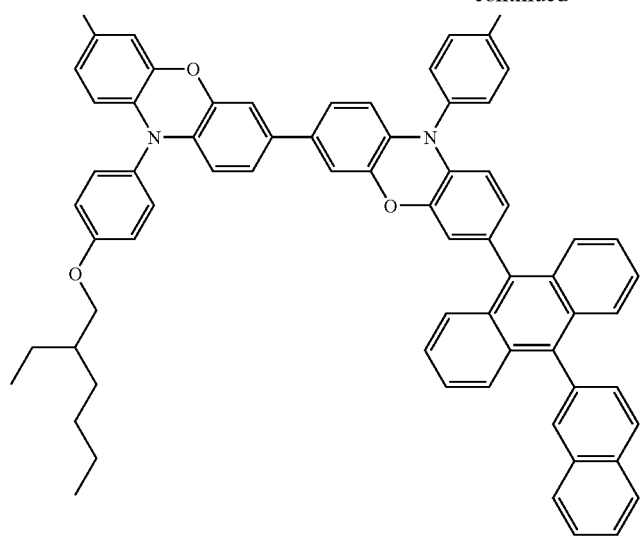
(7)
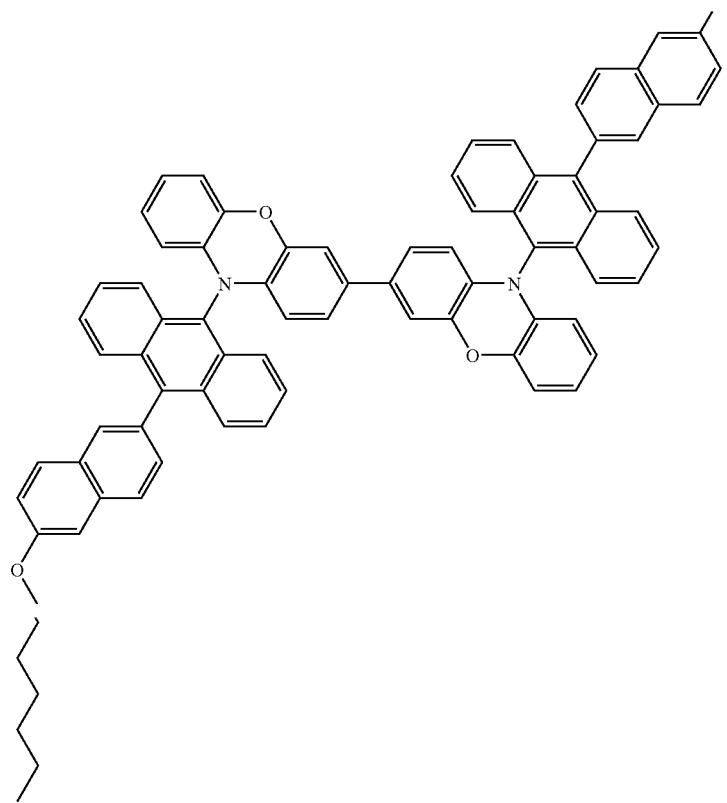

-continued
(8)
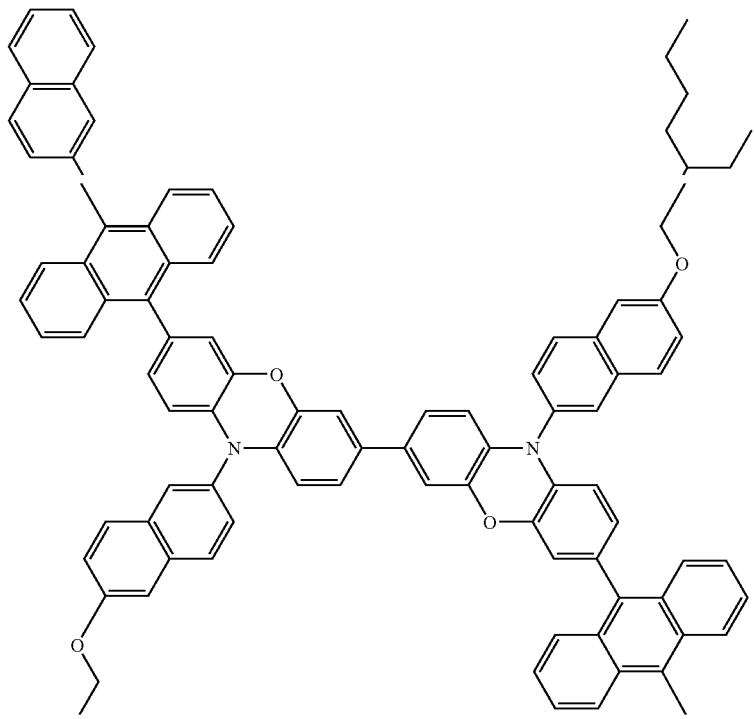
(9)
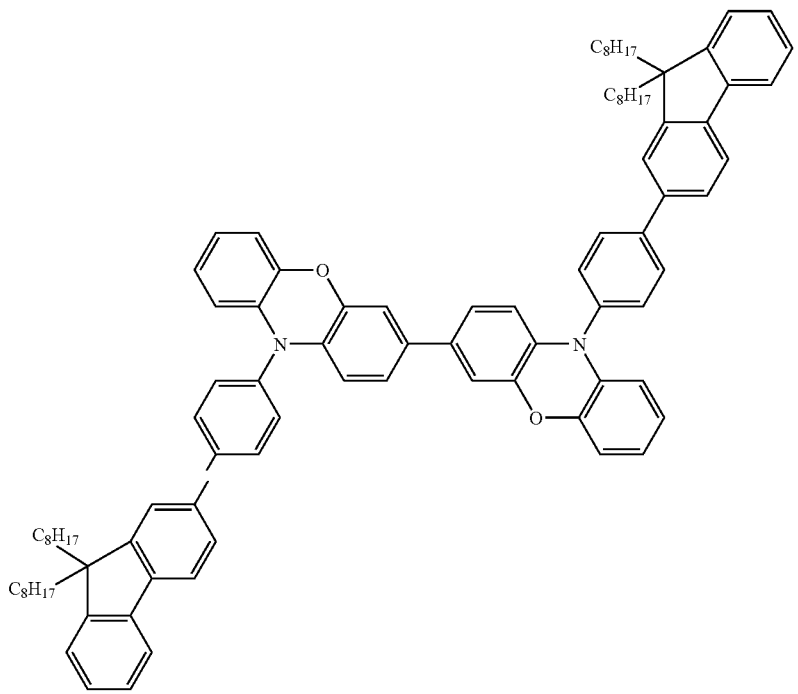

A method of preparing an organic electroluminescent compound according to an embodiment of the present invention, for example, having Formula 2, will now be described.

First, a phenoxazine-based compound (PY) represented by Formula (2) is synthesized as shown in scheme 1:

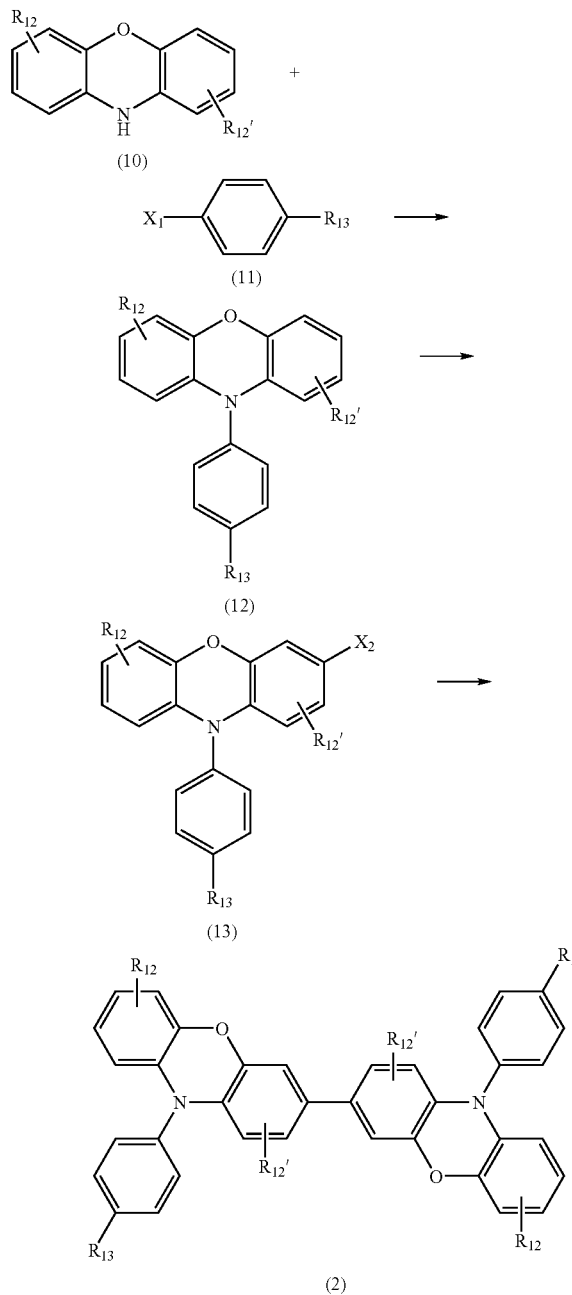

wherein each of $R_{12}$, $R_{12}'$, and $R_{13}$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group; and each of $X_1$ and $X_2$ is a halogen atom.

Referring to scheme 1, phenoxazine derivative represented by Formula 10 is reacted with compound represented by Formula 11 in the presence of a catalytic composition comprising a transition metal, for example, palladium, and a ligand compound, thereby obtaining compound (PO) represented by Formula 12.

Subsequently, the compound represented by Formula 12 is halogenated by adding an equal equivalent of halogen thereto in the presence of a polar organic solvent, for example, chloroform and dimethylformamide, and thus compound represented by Formula 13 is obtained.

Next, the compound represented by Formula 13 is subjected to a dehalogenation reaction and a dimerization reaction of a phenoxazine derivative in the presence of a catalyst and an organic solvent in a reactor, which is evacuated and refluxed with nitrogen gas, thereby obtaining compound represented by Formula 2.

Other organic electroluminescent compounds according to embodiments of the present invention may be synthesized in a similar way to the method described above.

Examples of a unsubstituted alkyl group as a substituent in the compound according to an embodiment of the present invention include methyl, ethyl, propyl, isobutyl, sec-butyl, pentyl, iso-amyl, hexyl, etc., wherein at least one hydrogen atom of the alkyl group may be substituted with a halogen atom, a hydroxy group, a nitro group, a cyano group, a substituted or unsubstituted amino group, such as —$NH_2$, —NH(R) or —N(R')(R'') where each of R, R' and R'' is independently a C1-C10 alkyl group, an amidino group, hydrazine, hydrazone, a carboxy group, a sulfonic acid group, a phosphoric acid group, a C1-C20 alkyl group, a C1-C20 halogenated alkyl group, a C1-C20 alkenyl group, a C1-C20 alkynyl group, a C1-C20 heteroalkyl group, a C6-C20 aryl group, a C6-C20 arylalkyl group, a C6-C20 heteroaryl group, or a C6-C20 heteroarylalkyl group.

The aryl group as a substituent in the compound according to an embodiment of the present invention includes a carbocyclic aromatic system containing at least one aromatic ring wherein such aromatic rings may be attached together in a pendent manner or may be fused. Examples of the aryl group include aromatic groups, such as phenyl, naphthyl, and tetrahydronaphthyl, etc. At least one hydrogen atom of the aryl group can be substituted with any substituent described above for the alkyl group.

The heteroaryl group as a substituent in the compound according to an embodiment of the present invention includes a 5-30 membered aromatic ring system containing one, two, or three hetero atoms selected from N, O, P, and S and having at least one ring wherein such rings may be attached together in a pendent manner or may be fused. At least one hydrogen atom of the heteroaryl group can be substituted with any substituent described above for the alkyl group.

The alkoxy group as a substituent in the compound according to an embodiment of the present invention includes a radical —O-alkyl, wherein the alkyl group is as defined above. Examples of the alkoxy group include methoxy, ethoxy, propoxy, isobutyloxy, sec-butyloxy, pentyloxy, iso-amyloxy, and hexyloxy, etc, wherein at least one hydrogen atom of the alkoxy group can be substituted with any substituent described above for the alkyl group.

The arylalkyl group as a substituent in the compound according to an embodiment of the present invention includes the above-defined aryl group in which hydrogen atom(s) is substituted with a lower alkyl group, for example, methyl, ethyl, or propyl. Examples of the arylalkyl group include benzyl and phenylethyl, etc. At least one hydrogen atom of the arylalkyl group can be substituted with any substituent described above for the alkyl group.

The heteroarylalkyl group as a substituent in the compound according to an embodiment of the present invention includes the above-defined heteroaryl group in which hydrogen atom(s) is substituted with a lower alkyl group. At least one hydrogen atom of the heteroarylalkyl group can be substituted with any substituent described above for the alkyl group.

The aryloxy group as a substituent in the compound according to an embodiment of the present invention includes a radical —O-aryl wherein the aryl group is as defined above. Examples of the aryloxy group include phenoxy, naphthoxy, anthracenyloxy, phenanthrenyloxy, fluorenyloxy, and indenyloxy, etc. At least one hydrogen atom of the aryloxy group can be substituted with any substituent described above for the alkyl group.

The heteroaryloxy group as a substituent in the compound according to an embodiment of the present invention includes a radical —O-heteroaryl wherein the heteroaryl group is as defined above. Examples of the heteroaryloxy group include benzyloxy and phenylethyloxy, etc. At least one hydrogen atom of the heteroaryloxy group can be substituted with any substituent described above for the alkyl group.

The cycloalkyl group as a substituent in the compound according to an embodiment of the present invention includes a C5-C30 monovalent monocyclic system wherein at least one hydrogen atom can be substituted with any substituent described above for the alkyl group.

The heterocycloalkyl group as a substituent in the compound according to an embodiment of the present invention includes a 5-30 membered monovalent cyclic system containing one, two, or three hetero atoms selected from N, O, P, and S. At least one hydrogen atom of the heterocycloalkyl group can be substituted with any substituent described above for the alkyl group.

The amino group as a substituent in the compound according to an embodiment of the present invention includes —$NH_2$, —NH(R), or —N(R')(R'') where each of R, R' and R'' is a C1-C10 alkyl group.

An organic electroluminescent device using the organic electroluminescent compound having Formula 1 and a method of manufacturing the device will now be described.

FIGS. 1A through 1F are schematic cross-sectional views illustrating laminated structures of organic electroluminescent devices according to embodiments of the present invention.

Referring to FIG. 1A, a light-emitting layer 12 containing the blue electroluminescent compound having Formula 1 is formed on a first electrode 10 and a second electrode 14 is formed on the light-emitting layer 12.

Figure 1B:
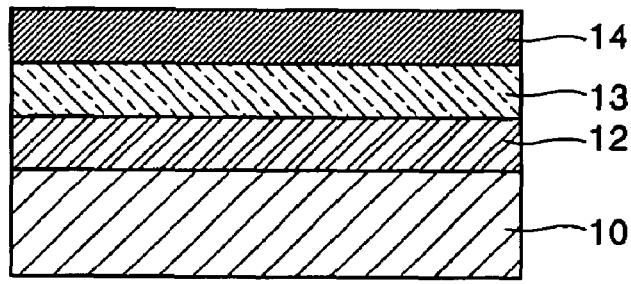

Referring to FIG. 1B, a light-emitting layer 12 containing the blue electroluminescent compound having Formula 1 is formed on a first electrode 10, a hole blocking layer (HBL) 13 is formed on the light-emitting layer 12, and a second electrode 14 is formed on the HBL 13.

Figure 1C:
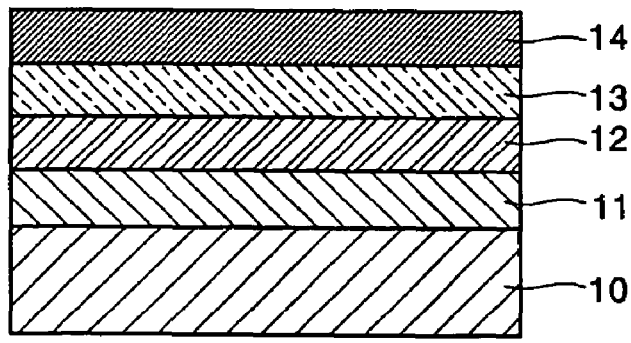

An organic electroluminescent device illustrated in FIG. 1C has the same laminated structure as that illustrated in FIG. 1B, except that a hole injection layer (HIL) 11 (also referred to as a buffer layer) is further formed between a first electrode 10 and a light-emitting layer 12.

Figure 1D:
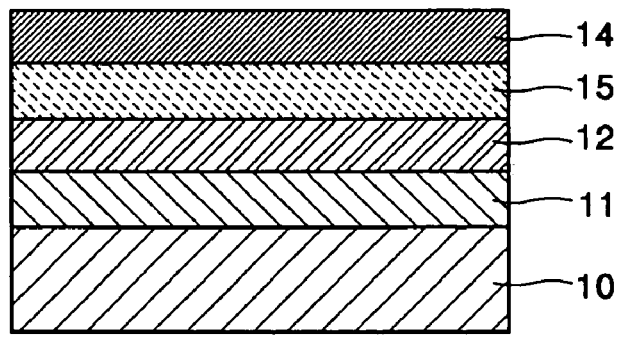

An organic electroluminescent device illustrated in FIG. 1D has the same laminated structure as that illustrated in FIG. 1C, except that an electron transport layer (ETL) 15, instead of the HBL 13, is formed on the light-emitting layer 12.

Figure 1E:
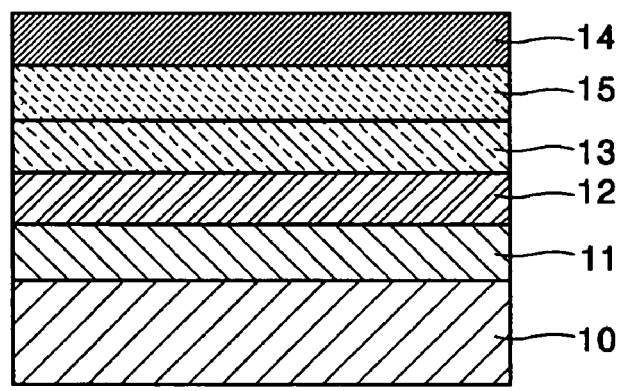

An organic electroluminescent device illustrated in FIG. 1E has the same laminated structure as that illustrated in FIG. 1C, except that a double layer having an HBL 13 and an ETL 15 sequentially laminated, instead of the HBL 13, is formed on the light-emitting layer 12.

Figure 1F:
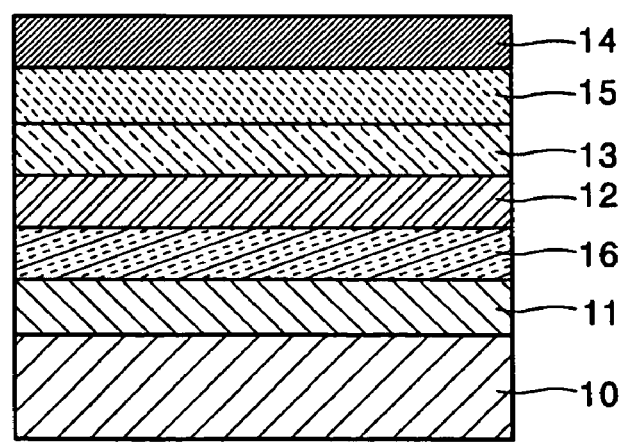

An organic electroluminescent device illustrated in FIG. 1F has the same laminated structure as that illustrated in FIG. 1E, except that a hole transport layer (HTL) 16 is further formed between the HIL 11 and the light-emitting layer 12. The HTL 16 prevents impurities in the HIL 11 from penetrating into the light-emitting layer 12.

The organic electroluminescent device according to an embodiment of the present invention may be manufactured by, but not limited to, conventional methods.

A method of manufacturing an organic electroluminescent device according to an embodiment of the present invention will now be described.

First, a first electrode 10 is patterned on a substrate (not shown). The substrate is a conventional substrate used in an organic electroluminescent device and may be a glass substrate or a transparent plastic substrate, which has excellent transparency, surface smoothness, easy handling, and excellent waterproofness. The substrate may have a thickness of 0.3-1.1 mm.

When the first electrode 10 is an anode, it is made of a conductive metal capable of easily injecting holes or an oxide thereof. Examples of the material for the first electrode 10 include ITO (iIndium tin oxide), IZO (indium zinc oxide), nickel (Ni), platinum (Pt), gold (Au) and iridium (Ir).

The substrate having the first electrode 10 formed thereon is cleaned, and then treated with UV/$O_3$. In the cleaning of the substrate, an organic solvent such as isopropanol (IPA) or acetone is used.

An HIL 11 is selectively formed on the first electrode 10 of the cleaned substrate. When the HIL 11 is formed on the first electrode 10, a contact resistance between the first electrode 10 and a light-emitting layer 12 decreases and a capability of the first electrode 10 to transport holes to the light-emitting layer 12 increases, thereby improving the driving voltage and lifetime of the device. A material for forming the HIL 11 may be any material commonly used in the art. Examples of the material for forming the HIL 11 include {poly(3, 4-ethylenedioxythiophene)} (PEDOT)/polystyrene parasulfonate (PSS), starburst materials, copper phthalocyanine, polythiophene, polyaniline, polyacetylene, polypyrrole, polyphenylene vinylene, or derivatives of these compounds. The material for the HIL 11 is spin coated on the first electrode 10 and dried, thereby forming an HIL 11. The HIL 11 may have a thickness of 300 to 2,000 Å, preferably 500 to 1100 Å. If the thickness of the HIL 11 is not in the range specified above, the hole injection capability is poor and the drying may be performed at 100 to 250° C.

The light-emitting layer 12 is formed by spin coating a composition for forming a light-emitting layer on the HIL 11 and drying the coating. The light-emitting layer forming composition may comprise 0.01 to 20% by weight of the compound having Formula 1 based on the weight of a host. Examples of the host include arylamine, a peryl compound, a pyrrole compound, a hydrazone compound, a carbazole compound, a stilbene compound, a starburst compound, an oxadiazole compound, etc. Any solvent that can dissolve the light-emitting compound can be used as a solvent in the composition. Examples of the solvent include toluene, chlorobenzene, etc.

A thickness of the light-emitting layer 12 may be adjusted to 100 to 1,000 Å, preferably 500 to 1,000 Å, by controlling the concentration of the light-emitting layer forming composition and the spin speed during the spin coating. If the thickness of the light-emitting layer 12 is less than 100 Å, a luminous efficiency of the device decreases. If the thickness of the light-emitting layer 12 is greater than 1,000 Å, the driving voltage of the device increases.

An HTL 16 may be selectively formed between the HIL 11 and the light-emitting layer 12. Any material having hole transporting capability can be used as a material for forming the HTL 16. Examples of the material for forming the HTL 16 include polytriphenylamine, etc. The HTL 16 may have a thickness of 100 to 1,000 Å.

An HBL 13 and/or an ETL 15 may be formed on the light-emitting layer 12 by evaporation or spin coating. The HBL 13 prevents excitons formed in the light-emitting material from moving to the ETL 15 or prevents holes from moving to the ETL 15.

Examples of a material for forming the HBL 13 include LiF, $MgF_2$, a phenanthroline compound represented by Formula 14, e.g., BCP manufactured by UDC Co., Ltd., an imidazole compound represented by Formula 15, a triazole compound represented by Formula 16, an oxadiazole compound represented by Formula 17, e.g., PBD, and an aluminum complex manufactured by UDC Co., Ltd., and Balq represented by Formula 14:

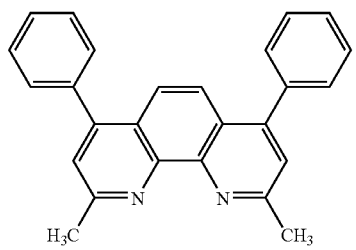

(14)

Phenanthroline-containing organic compound

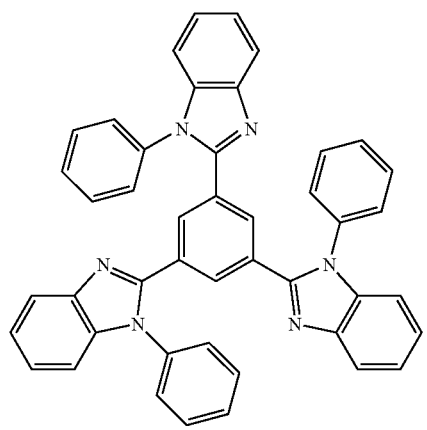

(15)

Imidazole-containing organic compound

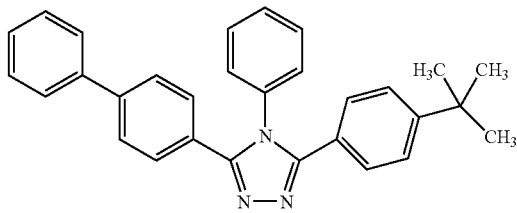

(16)

Triazole-containing organic compound

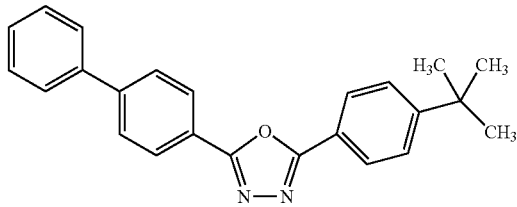

(17)

Oxadiazole-containing organic compound

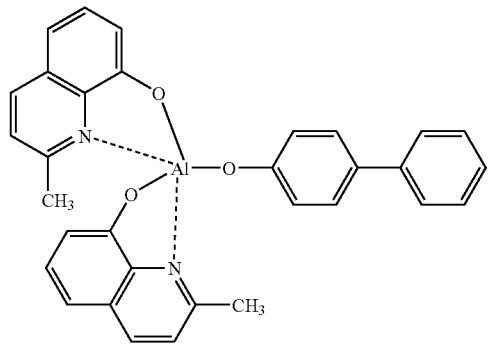

(18)

BAlq

Examples of a material for forming the ETL 15 include an oxazole compound, an isoxazole compound, a triazole compound, an isothiazole compound, an oxadiazole compound, a thiadiazole compound, a perylene compound represented by Formula 19, an aluminum complex, e.g., Alq3 (tris(8-quinolinolato)-aluminum) represented by Formula 20, BAlq represented by Formula 18, SAlq represented by Formula 21, or Almq3 represented by Formula 22, and a gallium complex, e.g., Gaq'2OPiv represented by Formula 23, Gaq'2OAc represented by Formula 24, or 2(Gaq'2) represented by Formula 25:

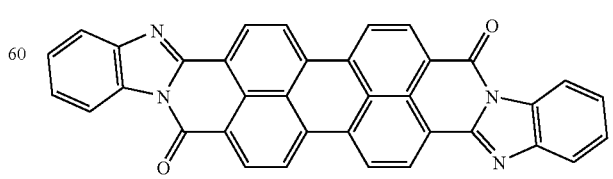

(19)

Perylene compound

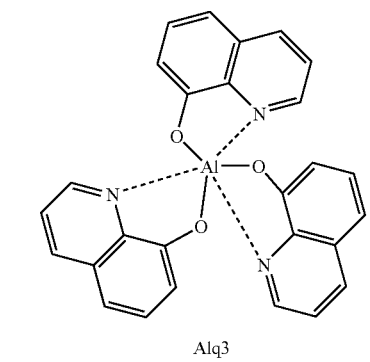
Alq3

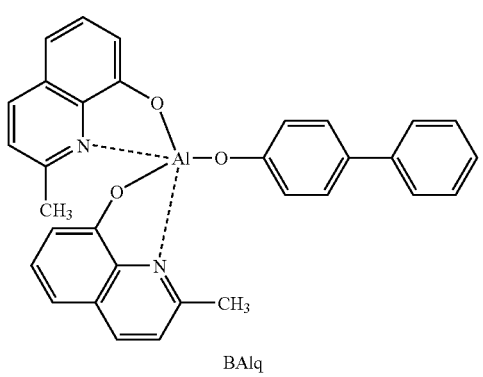
BAlq

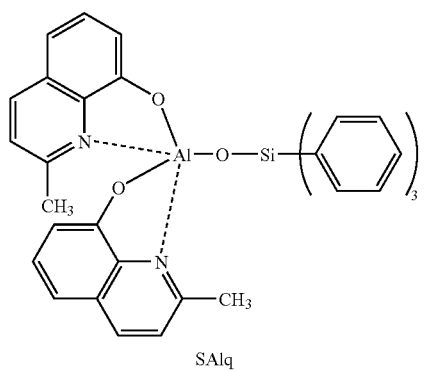
SAlq

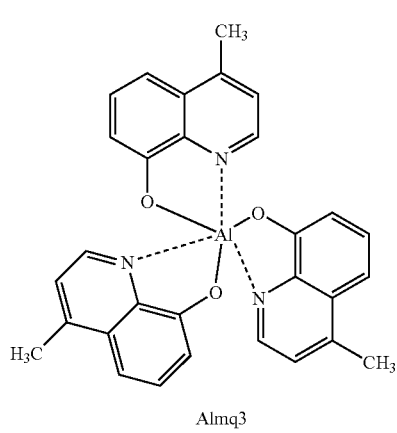
Almq3

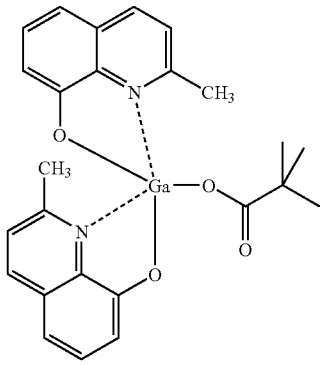
Gaq'2OPiv

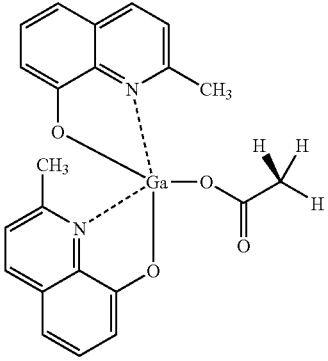
Gaq'2Oac

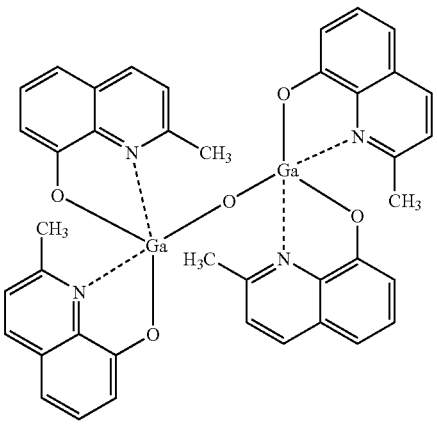
2(Gaq'2)

The HBL 13 may have a thickness of 100 to 1,000 Å, and the ETL 15 may have a thickness of 100 to 1,000 Å. If the thicknesses of the HBL 13 and the ETL 15 are not in the ranges specified above, hole blocking capability and electron transport capability are poor.

Then, a second electrode 14 is formed on the resultant product, followed by encapsulating, thereby completing an organic electroluminescent device.

The second electrode 14 may be formed by depositing a metal having a low work function, for example, Li, Ca, Ca/Al, LiF/Ca, LiF/Al, Al, Mg, and Mg alloy. The second electrode 14 may have a thickness of 50 to 3,000 Å.

The compound having Formula 1 according to an embodiment of the present invention may be used not only as the material for forming a light-emitting layer in manufacturing the organic electroluminescent device, but also as the material for forming an HTL. Also, the compound having Formula 1 may be used as an intermediate in bio-field.

The organic electroluminescent device according to an embodiment of the present invention may be manufactured by conventional methods using a light-emitting compound, without a need for any special apparatus or method.

Hereinafter, the present invention will be described in more detail with reference to the following examples. However, these examples are given for the purpose of illustration and are not intended to limit the scope of the invention.

Synthesis Example: Synthesis of phenoxazine dimer (PY, having Formula 3)

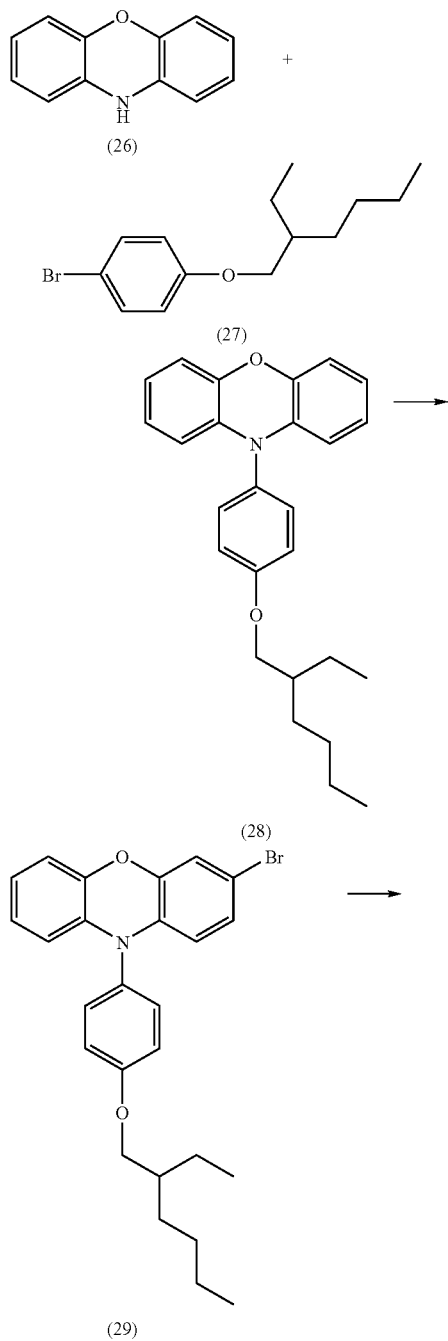

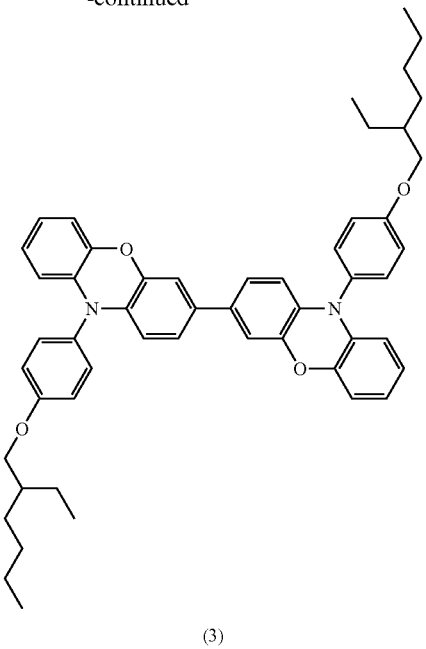

Synthesis of Compound of Formula 27

48.4 g (0.35 mole) of $K_2CO_3$ was added to a solution of 50 g (0.29 mole) of 4-bromophenol in 500 mL of acetone, and 73.3 g (0.38 mole) of 1-bromooctane was added to the mixture and refluxed for 24 hours.

After the reaction was completed, the resultant product was extracted using a 2:1 mixture of water and $CHCl_3$ by volume to remove $K_2CO_3$. The organic layer was dried over $MgSO_4$, concentrated, and subjected to silica gel column chromatography using hexane as an eluent. The resultant eluate was distilled under reduced pressure to remove unreacted 1-bromooctane. Thus, 80 g of compound of Formula 27 was obtained (yield: 96%). The structure of compound of Formula 27 was identified by $^1$H-NMR.

(2) Synthesis of Compound of Formula 28 (PO)

18 g (64 mmol) of compound of Formula 27, 10 g (54 mmol) of phenoxazine of Formula 26, 7.4 g (77 mmol) of sodium tert-butoxide, 0.61 g (1.1 mmol) of $Pd_2(dba)_3$ [(tris (dibenzylidine acetone) dipalladium(0))], and 0.22 g (1.1 mmol) of tri(tert-butyl)phosphine were dissolved in 250 mL of xylene and reacted at 80° C. for 12 hours.

After the reaction was completed, the resultant product was cooled to room temperature, and 200 mL of distilled water was added to the mixture. Then, the mixture was extracted with a 1:1 mixture of xylene and water by volume. The organic layer was dried over $MgSO_4$, concentrated, and subjected to silica gel column chromatography using a 1:2 mixture of toluene and hexane by volume as an eluent. The resultant eluate was concentrated and dried to obtain 18.5 g of compound of Formula 28 (yield: 88%). The structure of compound of Formula 28 was identified by $^1$H-NMR.

(3) Synthesis of Compound of Formula 29

1 equivalent of bromine was slowly added to a solution of 5 g (13 mmol) of compound of Formula 28 in 150 ml of $CHCl_3$ while maintaining the temperature at 0° C. When the complete consumption of the starting material was confirmed by thin layer chromatography (TLC), the addition of bromine was stopped, and the mixture was stirred for 10 min.

Next, a small amount of acetone was added to the mixture to quench bromine, and extracted with a 2:1 mixture of water and CHCl$_3$ by volume. The organic layer was dried over MgSO$_4$, concentrated, and reprecipitated in methanol to obtain 6 g of compound of Formula 29 (yield: 85%). The structure of compound of Formula 29 was identified by $^1$H-NMR:

$^1$H-NMR (300 MHz, CDCl3): δ 0.91(m, 6H ), δ 1.45(m, 8H ), δ 1.82(m, 1 H), δ 3.89(d, 2H ), δ 5.82(d, 2H ), δ 6.5~7.5(m, 9H ).

(4) Synthesis of Compound of Formula 3 (PY)

A Schlenk flask was evacuated and refluxed with nitrogen gas several times to completely remove moisture. Then, 880 mg (3.2 mmol) of bis(1,5-cyclooctadiene)nickel(O) [hereinafter, referred to as Ni(COD)] and 500 mg (3.2 mmol) of bipyridal were charged into the Schlenk flask in a glove box, and the flask was evacuated and refluxed with nitrogen gas several times again. Next, 10 ml of anhydrous dimethylfuran (DFM), 346 mg (3.2 mmol) of 1,5-cyclooctadiene (COD), and 10 ml of anhydrous toluene were added to the flask under a nitrogen stream. After the mixture was stirred at 80° C. for 30 min, 0.746 g (0.16 mmol) of compound of Formula 29 was diluted with 10 ml of toluene and added to the mixture. Next, 10 ml of toluene was added to the mixture while washing materials adhered to the flask wall, and then the mixture was stirred at 80° C. for 2 hours. After the stirring of the mixture, the temperature of the mixture was cooled to 60° C. Then, the reaction mixture was poured into a mixture of HCl, acetone, and methanol (volume ratio 1:1:2) to form precipitates. The precipitates thus formed were dissolved in chloroform and the organic layer was dried over MgSO4, concentrated, and subjected to silica gel column chromatography using a 3:7 mixture of toluene and hexane by volume as an eluent. The resultant eluate was concentrated and dried to obtain 0.5 g of compound of Formula 3. The structure of compound of Formula 3 was identified by $^1$H-NMR:

1H-NMR (300 MHz, CDCl3): δ 0.93(m, 12H ), δ 1.48(m, 16H ), δ 1.80(m, 2H ), δ 3.92(d, 4H ), δ 5.85(d, 4H ), δ 6.3~7.7(m, 18H ).

Figure 2:
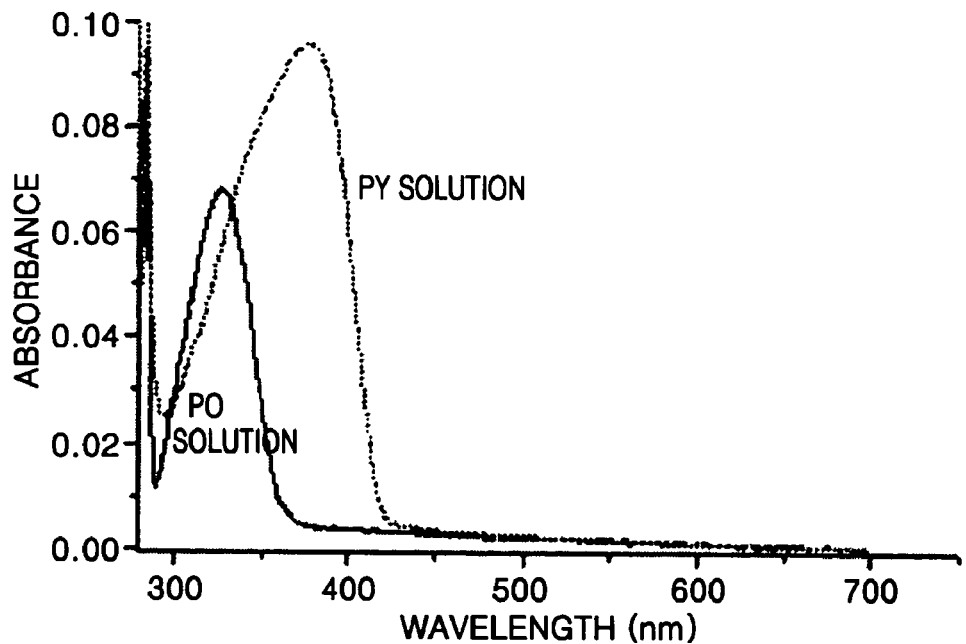
FIG. 2 is a UV absorption spectrum of the compound obtained in Synthesis Example.

The UV absorption spectrums and photoluminescent spectrums of solutions and films of compound (PO) of Formula 28 and its dimer, compound (PY) of Formula 3 as described above were examined and illustrated in FIGS. 2 through 4. FIG. 2 is a UV absorption spectrum of the compound obtained in Synthesis Example, and FIGS. 3 and 4 are photoluminescent spectrums of the compound obtained in Synthesis Example.

Figure 3:
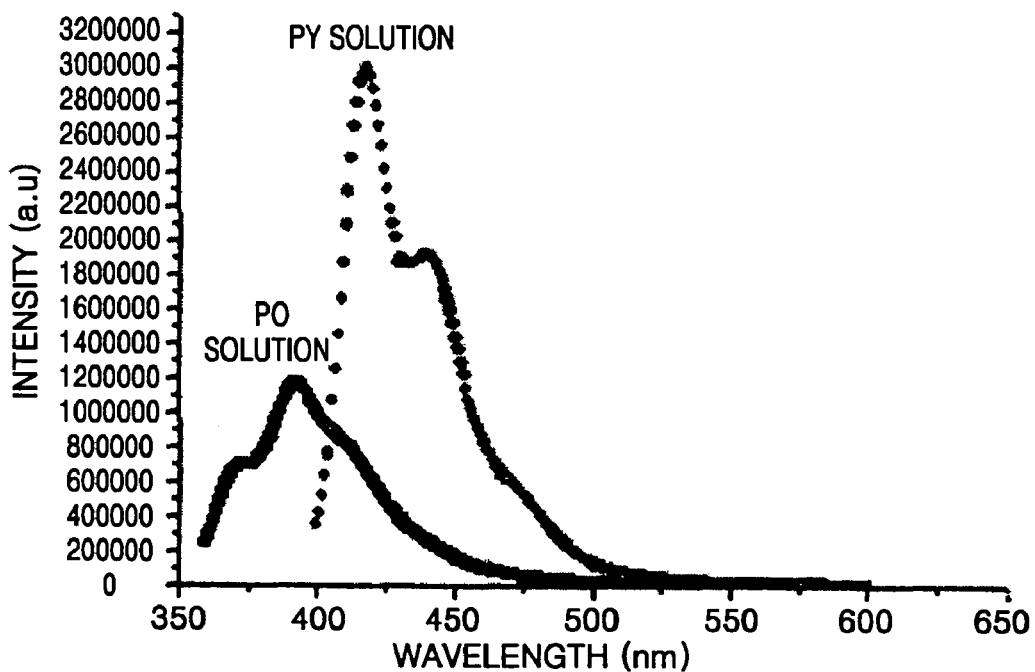
FIGS. 3 and 4 are photoluminescent spectrums of the compound obtained in Synthesis Example.
Figure 4:
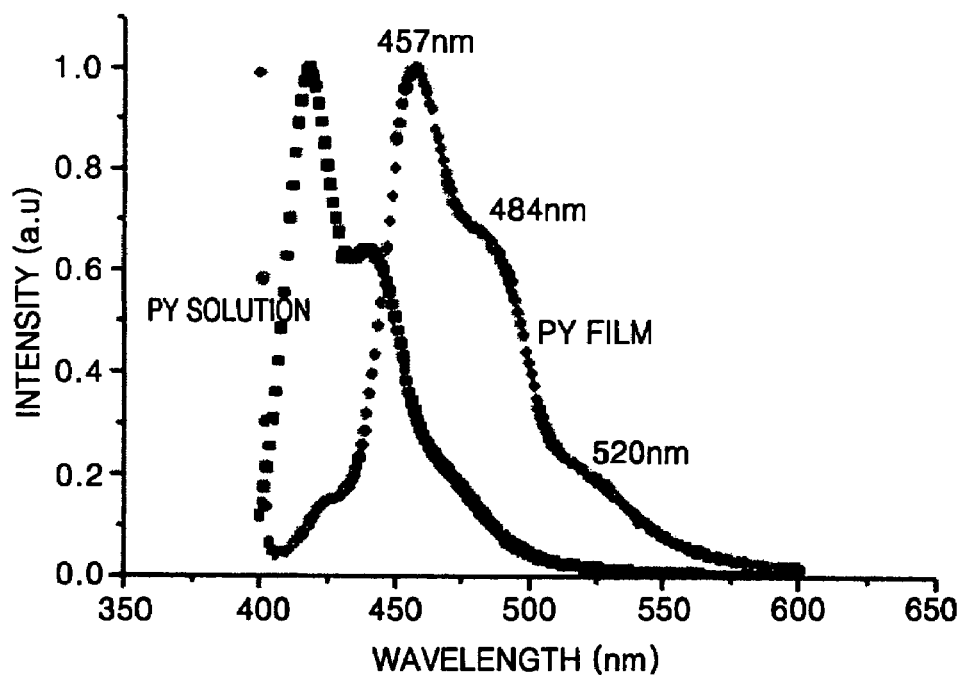

Referring to FIGS. 2 through 4, the dimer compound (PY) of Formula 3 according to an embodiment of the present invention had a blue electroluminescent property.

Example: Manufacture of Organic Electroluminescent Device

An electroluminescent device was manufactured using compound of Formula 3 obtained in Synthesis Example.

First, a transparent electrode substrate of glass coated with ITO (indium tin oxide) was cleaned. Then, the ITO was patterned by using a photoresist resin and an etchant, and the resulting substrate was cleaned again. Batron P 4083 (available from Bayer) as a conductive buffer layer was coated onto the substrate to a thickness of about 5 nm, and then baked at 180° C. for about 1 hour.

Then, 1% by weight of the compound having Formula 3 (PY) was dissolved in 99% by weight of toluene. Separately, 1% by weight of polyvinylcarbazole (PVK) was dissolved in 99% by weight of toluene. The obtained solutions were respectively filtered through a 0.2 mm filter and the filtrates containing PVK and PY, respectively, were mixed together in a weight ratio of 97:3 to obtain a mixed solution of PVK and PY, which was used as a composition for forming a light-emitting layer.

The mixed solution of PVK and PY was spin coated on the above buffer layer at 2500 rpm for 50 seconds and 150 rpm for 10 minutes. After baking the coated substrate, the solvent was removed in a vacuum oven to form a thin electroluminescent film with a thickness of 51 nm.

Then, LiF (thickness of 1 nm) and Al (thickness of 250 nm) were sequentially deposited on the thin film using a vacuum depositor under a vacuum of 4×10$^{-6}$ torr or less. When depositing, the thickness and the growth rate of the thin film were controlled using a crystal sensor.

Figure 5:
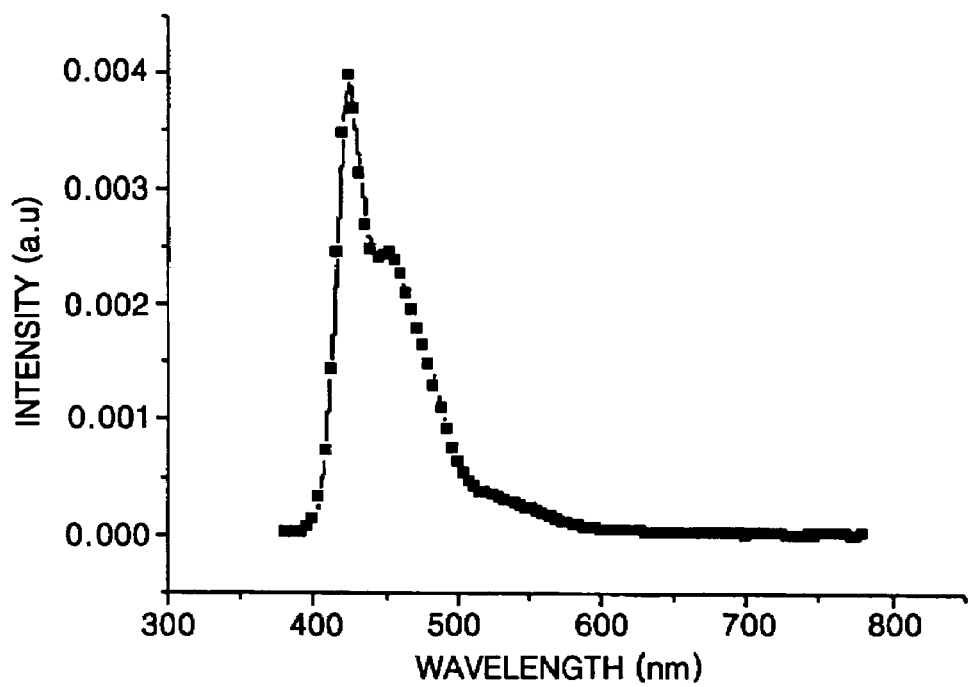
FIG. 5 is an electroluminescent spectrum of the organic electroluminescent device obtained in Example.

FIG. 5 is an electroluminescent spectrum of the organic electroluminescent device obtained in Example according to an embodiment of the present invention. Referring to FIG. 5, blue electroluminescence was confirmed.

Figure 6:
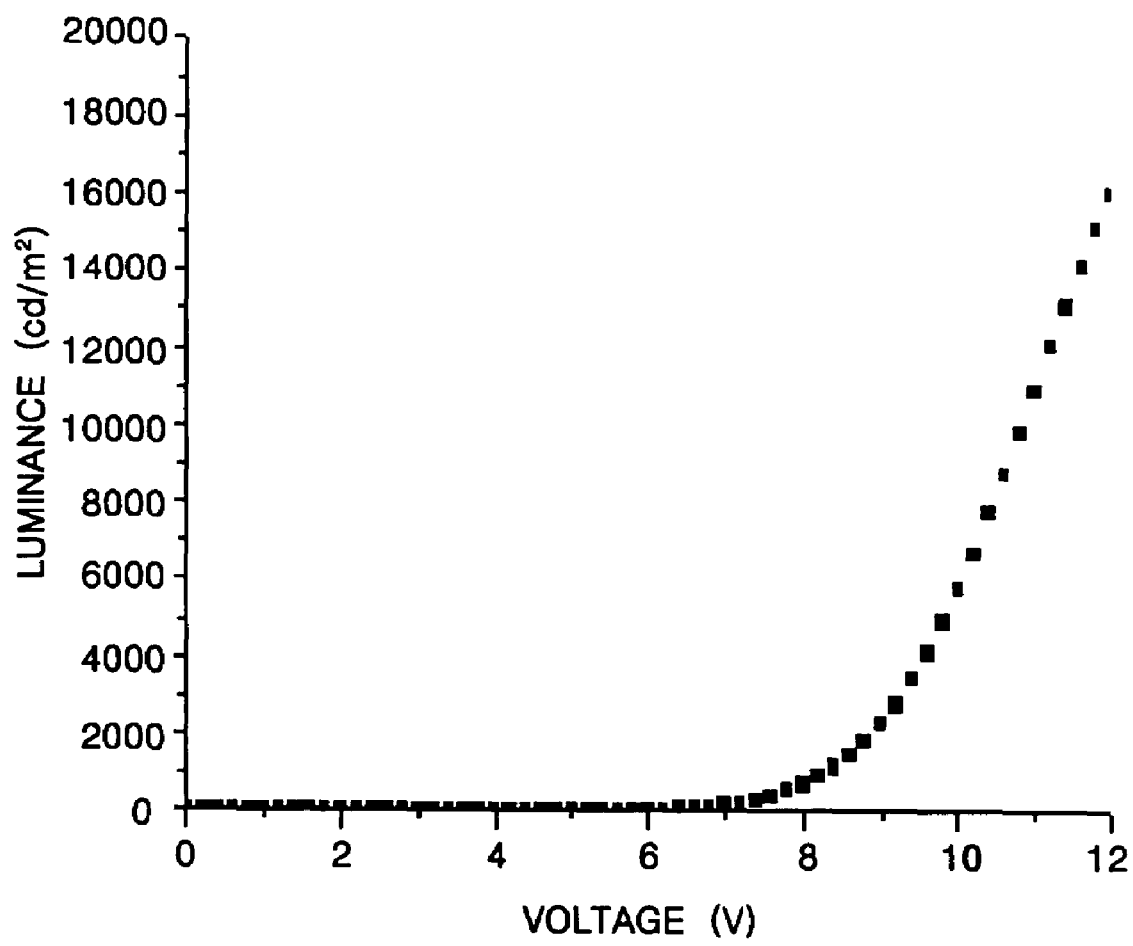
FIG. 6 is a graph of voltage vs. luminance of the organic electroluminescent device obtained in Example.

Luminance of the organic electroluminescent device obtained Example was examined. The results are illustrated in FIG. 6. In the evaluation, the forward bias voltage as a direct voltage was used for the driving voltage. The device showed typical properties of rectifying diodes. Especially, the device showed excellent stability, in that the initial voltage-current density characteristic was maintained even after driving had been repeated several times.

Referring to FIG. 6, the organic electroluminescent device obtained in Example had excellent luminance.

As described above, an organic electroluminescent compound according to the present invention has a blue electroluminescent property. The organic electroluminescent compound can easily transport charges, be used in dry and wet processes and have an excellent blue light-emitting property. An organic electroluminescent device having an organic layer containing the organic electroluminescent compound according to the present invention has improved color purity, efficiency, and luminance.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound having Formula 1: (1)

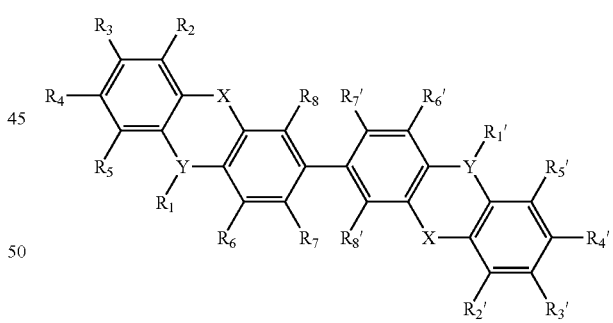

wherein each of R$_1$ through R$_8$ and R$_1$' through R$_8$' is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group;

X is Se; and

Y is N or P.

2. The compound of claim 1, wherein each of $R_1$ through $R_8'$ in Formula 1 is independently selected from the group consisting of Formulae (1a) through (1h):

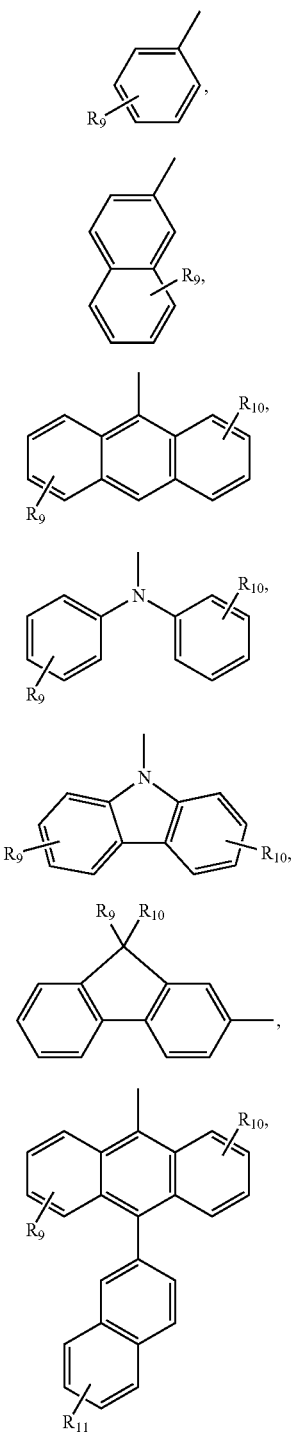

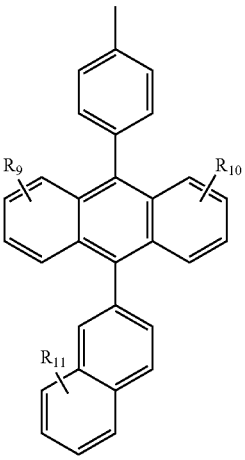

wherein each of $R_9$, $R_{10}$, and $R_{11}$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group.

3. An organic electroluminescent device having an organic layer comprising the compound of claim 1.

4. An organic electroluminescent device, comprising:
a pair of electrodes;
an organic layer between the pair of electrodes, the organic layer being a light-emitting layer comprising a phenoxazine dimer having Formula 1:

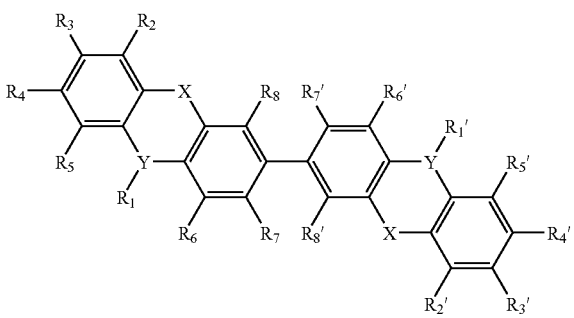

wherein each of $R_1$ through $R_8$ and $R_1'$ through $R_8'$ in Formula 1 is independently selected from the group consisting of Formulae (1a) through (1h):

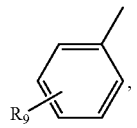

-continued

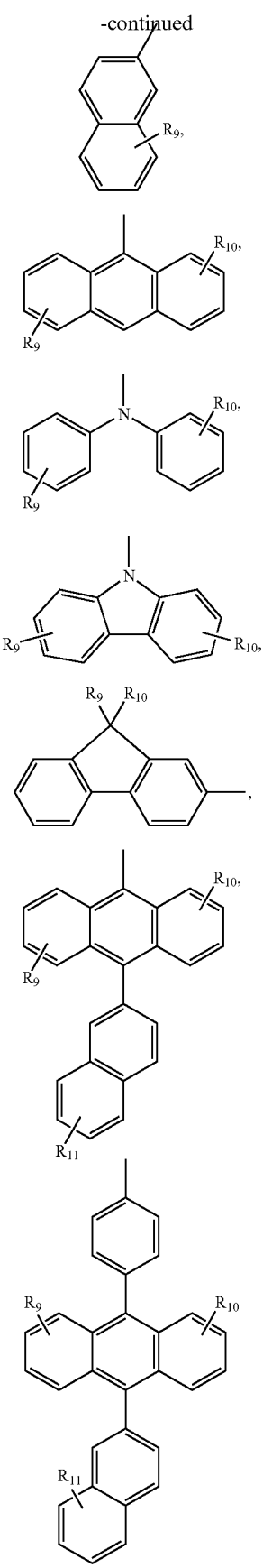

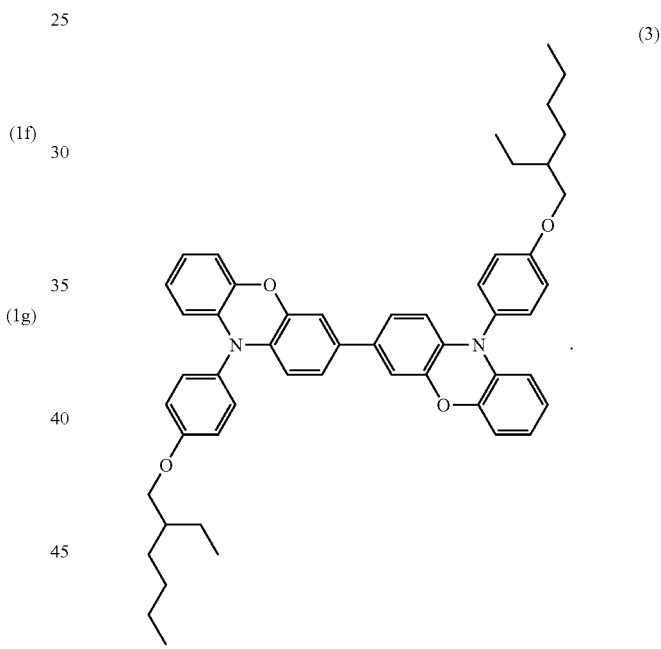

wherein each of $R_9$, $R_{10}$, $R_{11}$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group;

X is O; and

Y is N.

5. The organic electroluminescent device of claim 4, wherein the organic electroluminescent compound is represented by Formula 3:

6. The organic electroluminescent device of claim 4, wherein the light-emitting layer is formed by a light-emitting layer forming composition comprising 0.01 to 20% by weight of the phenoxazine dimer having Formula 1 based on the weight of a host.

7. An organic electroluminescent device, comprising:
   a first electrode;
   a second electrode;
   a light-emitting layer between the first electrode and the second electrode; and
   optionally a hole transport layer between the light-emitting layer and the first electrode, at least one of the light-emitting layer and the optional hole transport layer formed from a phenoxazine dimer represented by Formula 2:

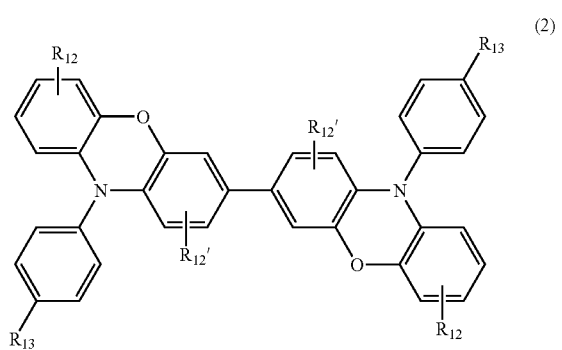

wherein each of $R_{12}$, $R_{12}'$ and $R_{13}$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group; and wherein the phenoxazine dimer is selected from the group consisting of Formulae 3 and 5 through 9:

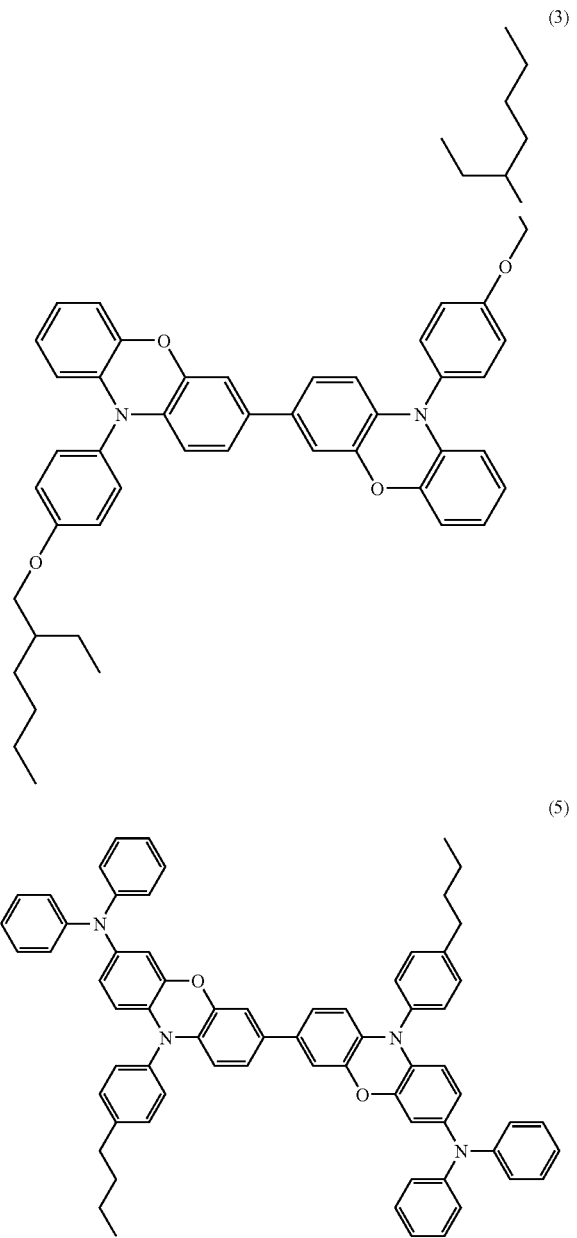

-continued
(6)
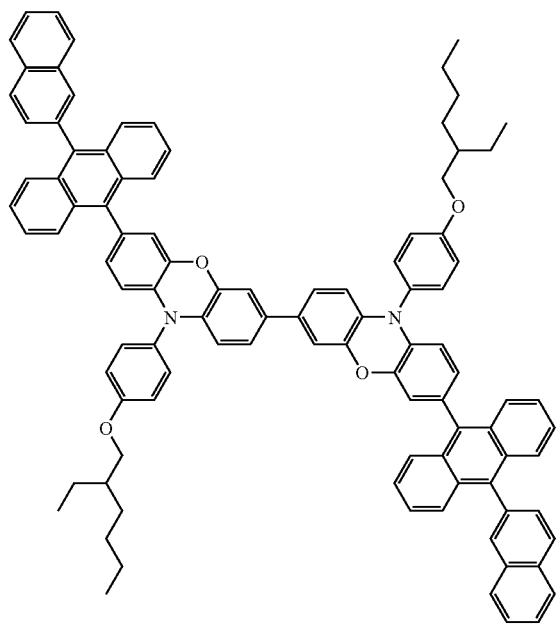
(7)
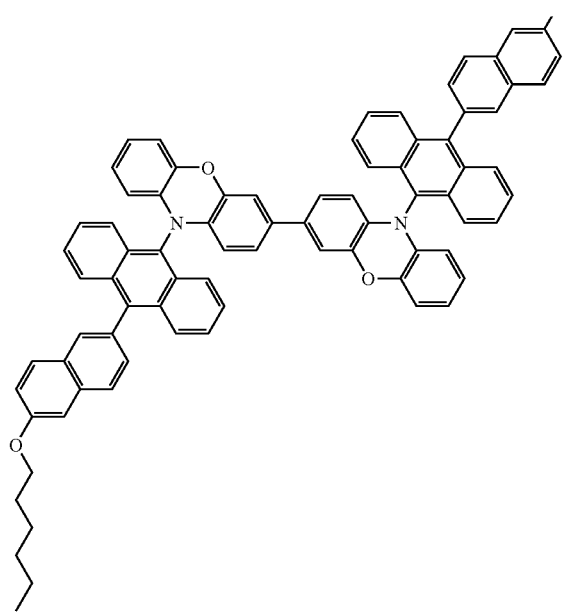

-continued
(8)
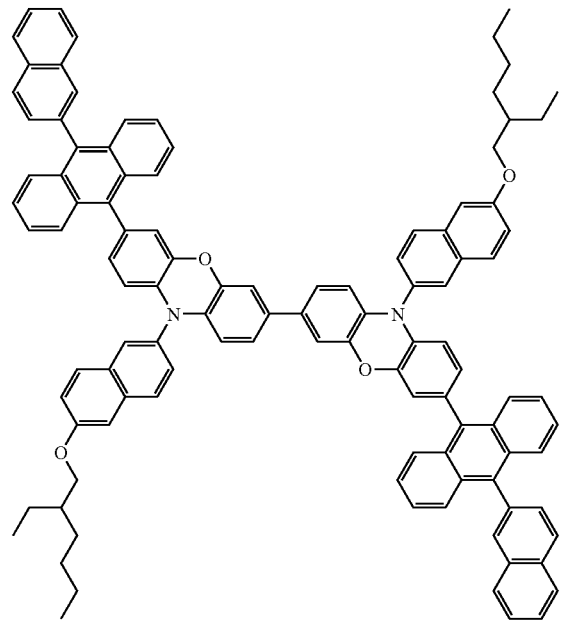
(9)
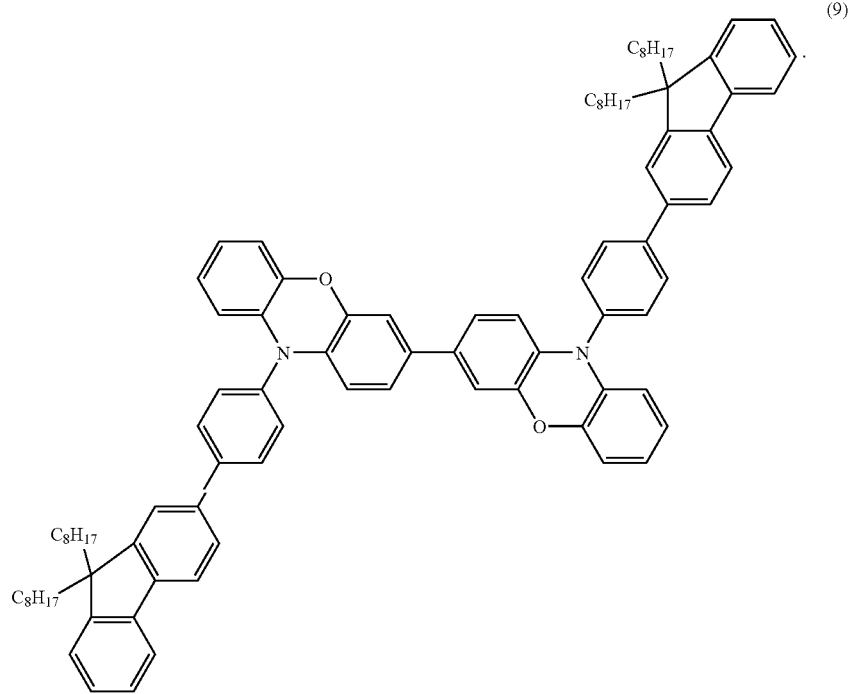

8. A compound having Formula 1:

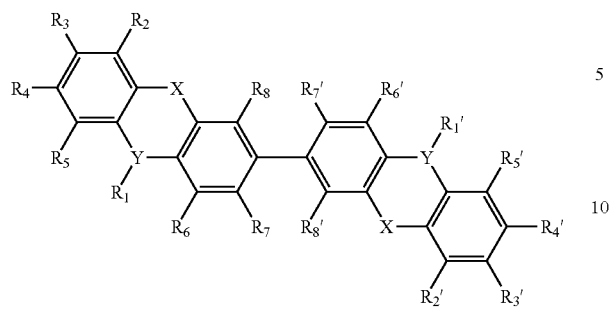
(1)

wherein each of $R_1$ through $R_8$ and $R_1'$ through $R_8'$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group;

X is O, S, or Se; and

Y is P.

9. The compound of claim 1, wherein each of $R_1$ through $R_8$ and $R_1'$ through $R_8'$ in Formula 1 is independently selected from the group consisting of Formulae (1a) through (1h):

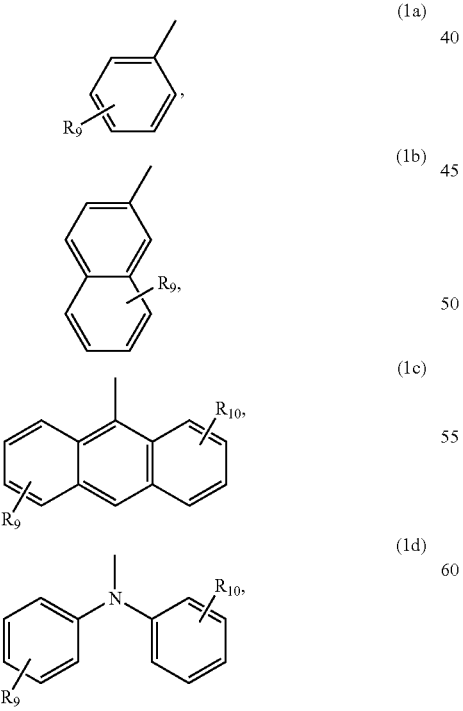

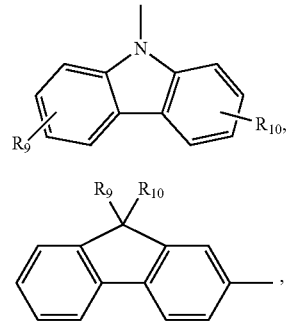
(1e)

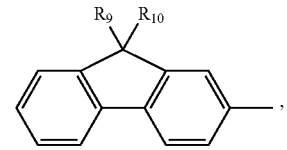
(1f)

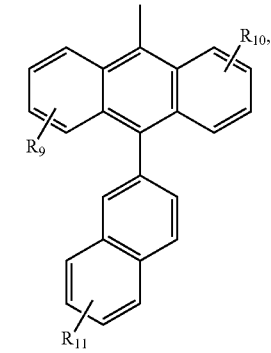
(1g)

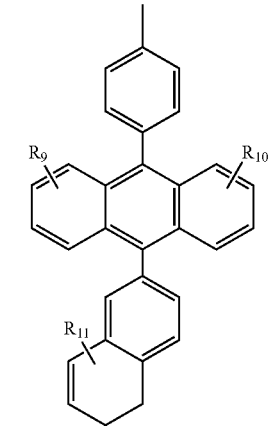
(1h)

wherein each of $R_9$, $R_{10}$, and $R_{11}$ is independently selected from the group consisting of a hydrogen atom, a halogen atom, a substituted or unsubstituted amino group, a cyano group, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C5-C30 heterocycloalkyl group, a substituted or unsubstituted C1-C30 alkyl ester group, and a substituted or unsubstituted C6-C30 aryl ester group.

10. An organic electroluminescent device having an organic layer comprising the compound of claim 8.

* * * * *